United States Patent [19]

Pepin et al.

[11] Patent Number: 5,614,136
[45] Date of Patent: Mar. 25, 1997

[54] PROCESS TO FORM DIMENSIONALLY VARIABLE TUBULAR MEMBERS FOR USE IN CATHETER PROCEDURES

[75] Inventors: Henry J. Pepin, Loretto; Michael S. Ferrandino, Elk River; Andrew G. Richardson, Chanhassen, all of Minn.

[73] Assignee: SciMed Life Systems, Inc., Maple Grove, Minn.

[21] Appl. No.: 398,213

[22] Filed: Mar. 2, 1995

[51] Int. Cl.$^6$ ................................. B29C 47/92
[52] U.S. Cl. .............. 264/40.3; 264/40.7; 264/149; 264/150; 264/171.26; 264/167; 425/140; 425/142; 425/145; 425/172; 425/380; 425/466; 425/467
[58] Field of Search ............... 264/40.3, 40.7, 264/149, 167, 150, 209.5, 210.2, 171.26; 425/325, 327, 380, 467, 140, 142, 145, 168–169, 170, 172, 466; 604/264

[56] References Cited

U.S. PATENT DOCUMENTS

| | | | |
|---|---|---|---|
| 2,940,126 | 6/1960 | Sheridan | 264/209.1 |
| 3,416,531 | 12/1968 | Edwards | 128/348 |
| 3,485,234 | 12/1969 | Stevens | 128/2 |
| 3,530,536 | 9/1970 | Thorman et al. | 425/168 |
| 3,674,404 | 7/1972 | Burlis et al. | 425/145 |
| 3,712,782 | 1/1973 | Burlis | 425/145 |
| 3,724,985 | 4/1973 | Burlis et al. | 425/380 |
| 3,752,617 | 8/1973 | Burlis et al. | 425/131 |
| 3,944,641 | 3/1976 | Lemelson | 264/70 |
| 4,044,765 | 8/1977 | Kline | 128/214.4 |
| 4,138,457 | 2/1979 | Rudd et al. | 264/167 |
| 4,282,876 | 8/1981 | Flynn | 128/349 R |
| 4,283,447 | 8/1981 | Flynn | 428/36 |
| 4,321,226 | 3/1982 | Markling | 264/139 |
| 4,330,497 | 5/1982 | Agdanowski | 264/150 |
| 4,551,292 | 11/1985 | Fletcher et al. | 264/139 |
| 4,577,543 | 3/1986 | Wilson | 87/11 |
| 4,596,563 | 6/1986 | Pande | 604/264 |
| 4,636,346 | 1/1987 | Gold et al. | 264/139 |
| 4,665,604 | 5/1987 | Dubowik | 29/415 |
| 4,690,175 | 9/1987 | Ouchi et al. | 138/131 |
| 4,738,666 | 4/1988 | Fuqua | 604/280 |
| 4,764,324 | 8/1988 | Burnham | 264/150 |
| 4,886,506 | 12/1989 | Lovgren et al. | 604/280 |
| 4,904,431 | 2/1990 | O'Maleki | 264/103 |
| 4,963,306 | 10/1990 | Weldon | 264/101 |
| 4,983,169 | 1/1991 | Furukawa | 604/164 |
| 5,045,072 | 9/1991 | Castillo et al. | 604/280 |
| 5,059,375 | 10/1991 | Lindsay | 264/167 |
| 5,069,673 | 12/1991 | Shwab | 604/280 |
| 5,088,991 | 2/1992 | Weldon | 604/280 |
| 5,248,305 | 9/1993 | Zdrahala | 604/280 |
| 5,250,034 | 10/1993 | Appling et al. | 604/164 |
| 5,371,934 | 12/1994 | Mang | 264/573 |

FOREIGN PATENT DOCUMENTS

| | | |
|---|---|---|
| 0618059A1 | 10/1994 | European Pat. Off. . |
| 0363953B1 | 12/1994 | European Pat. Off. . |
| 52-16570 | 2/1977 | Japan .................... 264/150 |
| WO93/00953 | 1/1993 | WIPO . |

*Primary Examiner*—Jeffery R. Thurlow
*Attorney, Agent, or Firm*—Nawrocki, Rooney & Sivertson, P.A.

[57] ABSTRACT

Process for forming a dimensionally variable tubular member for use in catheterization procedures. The process includes a mechanism for extruding a tubular member. A variable speed puller pulls the tubular member through or from the extrusion means at a selectively variable speed. A variable air or gas pressure supply supplies pressurized air or gas to the extrusion mechanism at a selectively variable rate. The dimensionally varying tubular member may be cut to desired lengths for use as catheter shafts or catheter soft tips. The process may include forming a tubular member having a dimensionally varying first layer and a dimensionally varying second layer, wherein a portion of the first layer at a distal end of the tubular member is removed.

19 Claims, 9 Drawing Sheets

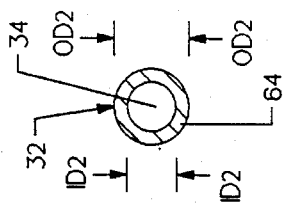
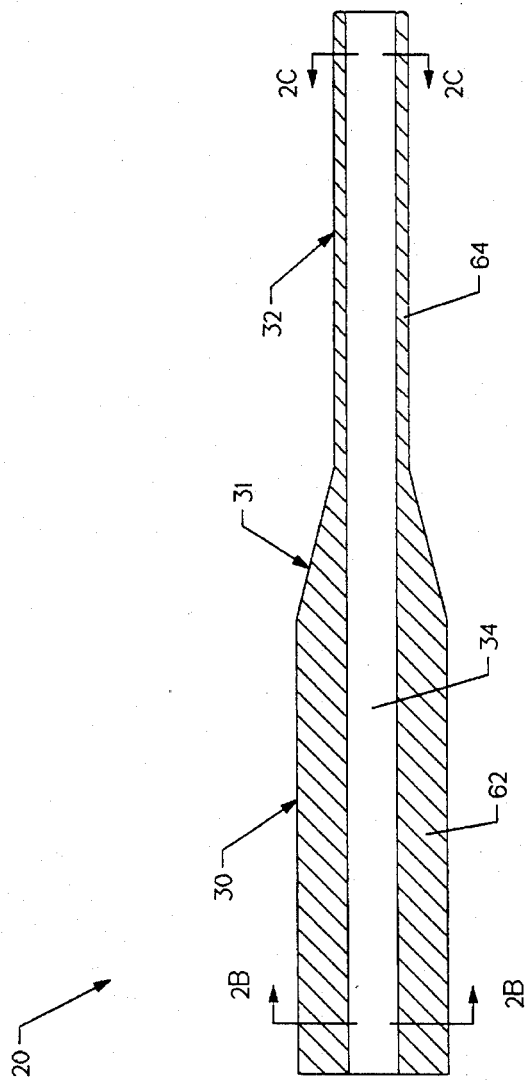
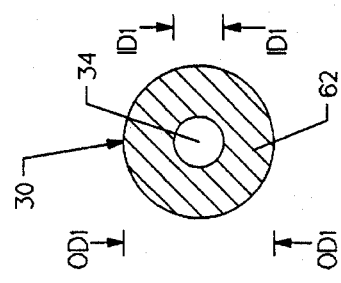

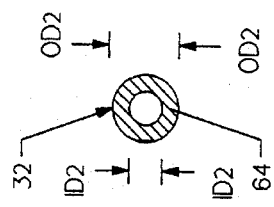
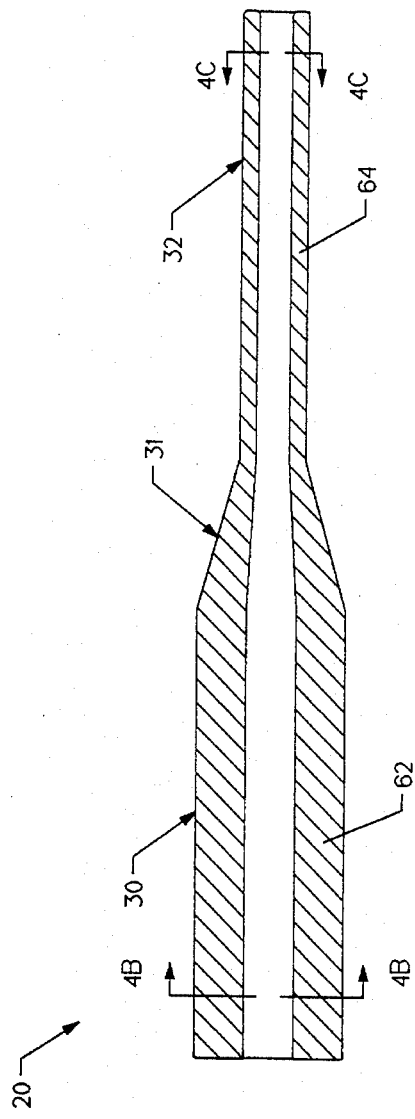
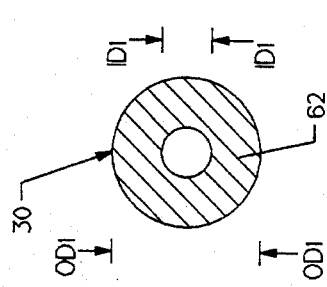
FIG. 4C
FIG. 4A
FIG. 4B
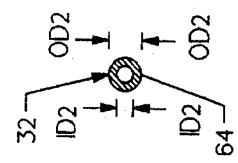
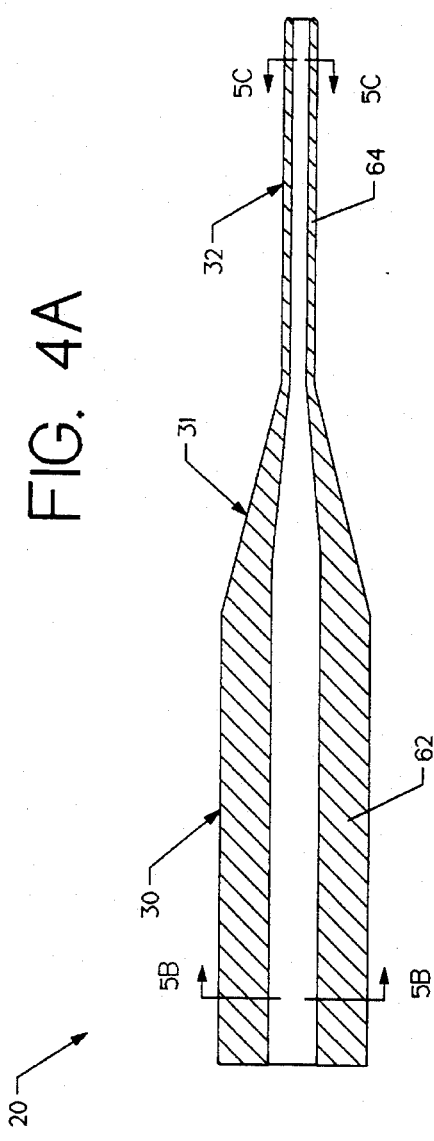
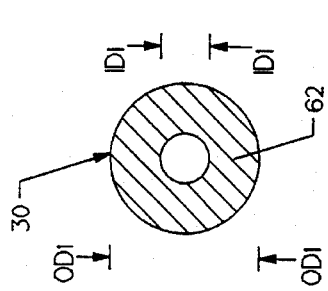
FIG. 5C
FIG. 5A
FIG. 5B

PROCESS TO FORM DIMENSIONALLY VARIABLE TUBULAR MEMBERS FOR USE IN CATHETER PROCEDURES

FIELD OF THE INVENTION

The present invention relates to guide, angiographic and diagnostic and dilatation catheters and method of manufacturing catheters. In particular, the present invention relates to a process for forming dimensionally variable tubular members for use in catheter procedures.

DESCRIPTION OF THE PRIOR ART

Guide catheters are well known for use in coronary catheterization and percutaneous transluminal coronary angioplasty (PTCA) procedures. In PTCA procedures, guide catheters aid in treatment of arterial lesions by providing a conduit for positioning dilatation balloon systems across an arterial stenosis. Additionally, guide catheters work with various assemblies for performing other medical and diagnostic procedures, such as dye delivery, arterial flushing, or arterial pressure monitoring.

Guide catheters include a shaft having a proximal and a distal end. A lumen extends longitudinally through the shaft from the proximal to the distal end. Operably connected to the proximal end of the shaft is a hub assembly, and connected to the distal end of the shaft is a soft tip.

In operation, the guide catheter is introduced over a guide wire into a previously placed femoral introducer sheath, and advanced up to the aortic arch. The guide wire is then removed. A Y-adapter and manifold assembly are attached to the guide catheter for implementation of diagnostic procedures, such as dye delivery, flushing capabilities and arterial pressure monitoring and for delivery of the balloon system. The guide catheter is advanced and maneuvered until the guide catheter soft tip is properly engaged in the ostium of the coronary to be dilatated.

The guide catheter soft tip includes a proximal section and an integrally formed distal section. A lumen extends longitudinally through both sections of the tip. The tip is formed of soft extruded polymeric material, such as a polyether blocked amide or PEBA, for atraumatic movement of the catheter through a patient's delicate arterial anatomy and for safer ostial engagement.

Additionally, the proximal end of the soft tip may be of a larger diameter than the distal end of the soft tip, for improved catheter steerability and safer ostial engagement. In the past, in order to vary the dimensional characteristics of the catheter tip, heat was applied to the tip. The heated tip was subsequently pulled and stretched to achieve the desired form.

Such heating and cooling methods resulted in reduced dimensional stability of the catheter tip. Heating and stretching the catheter tip alters the molecular structure of the catheter material, and correspondingly, changes the structural integrity and performance of the catheter.

One such method is suggested in U.S. Pat. No. 4,596,563 to Pande which suggests a thin walled multi-layered catheter having a fuseless tip. The catheter is formed by first extruding a rigid inner layer over a continuous mandrel. The extrusion process is stopped at predetermined gap lengths or the inner layer is removed at predetermined gap lengths. Next, a soft outer layer is extruded over the entire continuous mandrel. The predetermined gap areas having only a soft outer layer define the soft tip portion of the catheter. The tip portion, which varies in dimension, is formed by a procedure such as immersing the tip portion in boiling water and bending the tip to achieve the desired shape, before removal of the mandrel.

Other methods of guide catheter construction are used which result in a dimensionally uniform tubular member. U.S. Pat. No. 4,904,431 to O'Maleki suggests a process for manufacturing non-fused soft tip catheters from a continuously formed tubular member. The tubular member has an inner, rigid layer and a soft, outer layer. The tubular member is formed by extruding the inner layer and outer layer at varied rates over a wire mandrel, resulting in a more rigid catheter region forming the catheter body and a softer region forming the catheter tip. The guide catheter body and tip region are of a uniform outer diameter and have uniform inner lumen diameter.

The present invention includes a method of manufacturing a dimensionally variable tubular member for use in catheter procedures. The dimensionally variable tubular member improves catheter steerability and provides for safer ostial engagement, while maintaining its molecular structure and structural integrity.

SUMMARY OF THE INVENTION

The present invention relates to guide, angiographic and diagnostic and balloon dilatation catheters and method of manufacturing catheters. In particular, the present invention includes a process for forming a dimensionally variable continuous tubular member for use in catheterization procedures.

In one preferred embodiment, the process includes an extrusion mechanism for extruding a tubular member. Means are provided for selectively varying the inside diameter of the tubular member and means are provided for selectively varying the outside diameter of the tubular member. A variable speed puller pulls the tubular member from the extrusion mechanism at a selectively variable speed. Additionally, pressurized air or another gas is supplied to the extrusion mechanism at a selectively variable rate.

The process may include a cutter for selectively cutting the tubular member into desired lengths. In one embodiment, the tubular member is cut into lengths for use as catheter soft tips.

A control mechanism may be included for providing signals to the variable speed puller and pressurized air or gas supply. The signals are representative of the desired tubular member dimensional characteristics. Additionally, the control mechanism is programmable for achieving the desired exact dimensional characteristics. The controller may also control the timing of the cutting mechanism for cutting the tubular member into desired lengths and the rate at which material is pulled into the extrusion mechanism.

In one embodiment, the dimensionally varying tubular member includes a first portion and a second portion. The first portion has a first outside diameter formed by the pulling mechanism pulling the tubular member from the extrusion mechanism at a first speed. The second portion has a second outside diameter formed by the pulling mechanism pulling the tubular member through or from the extrusion mechanism at a second speed.

The first portion may have a first inside diameter formed by the air or gas supply supplying air or other gas to the extrusion mechanism at a first pressure or volume rate. The second portion has a second inside diameter formed by the air or gas supply supplying air or gas to the extrusion mechanism at a second pressure or volume rate.

In another embodiment, the present invention includes a process for forming a dimensionally variable continuous tubular member for use in catheterization procedures. The process includes the steps of forming a tubular member by passing the material through an extruder. The material is pulled from the extruder at a desired speed. Air or other gas is provided to the extruder from an air or gas supply. The speed at which the material is pulled from the extruder is changed, and the pressure or volume at which the air or gas is supplied to the extruder is changed.

The speed at which the material is pulled from the extruder may be selectively changed by a controller. In one embodiment, by changing the speed at which the material is pulled from the extruder, the outside diameter of the continuous tubular member is changed. The outside diameter of the continuous tubular member may be changed to a second outside diameter within a catheter length of one inch, but is not limited to one inch.

The change in pressure or volume at which the air is supplied to the extruder may be selectively controlled by a controller. In one embodiment, by changing the pressure or volume at which air is supplied to the extruder, the inside diameter of the tubular member is changed. The inside diameter of the tubular member may be changed to a second inside diameter within a catheter length of less than one inch. Additionally, the controller may control the timing of cutting the tubular member into desired lengths, and the amount of material entering the extruder.

It is recognized that the present invention may be used to manufacture dimensionally variable tubular members for use in manufacturing catheter shafts, catheter tips, fuseless catheter systems, and other products where dimensionally varying characteristics are desirable. The process of the present invention allows dimensionally variable tubular members to be formed to desired specifications to meet required operational and performance characteristics without sacrificing the structural integrity of the tubular member. Both the inside diameter and the outside diameter of the catheter may be varied to improve catheter performance characteristics and be compatible with other catheter diagnostic and PTCA systems.

In another embodiment, the present invention includes a process for forming a dimensionally variable tubular member having multiple layers for use with catheterization procedures. The process includes forming a dimensionally varying tubular first layer by controlling the speed at which the first layer is formed; forming a dimensionally varying tubular second layer over the first layer by controlling the speed at which the second layer is formed; and removing a portion of the first layer at a distal end of the tubular member. The process may further include forming a tubular member over a mandrel and forming a structural layer over the tubular member wherein the first layer is formed over the structural layer.

The above process may also include reforming the distal end of the tubular member. The tubular member distal end may be reformed through a heating process.

BRIEF DESCRIPTION OF THE DRAWINGS

The invention will be further described with reference to the accompanying drawings where like numbers refer to like parts in several views and wherein:

FIG. 2A is a cross-sectional view of a guide catheter tip taken along lines 2A—2A of FIG. 1;

FIG. 2B is a cross-sectional view of the proximal portion of a guide catheter tip taken along lines 2B—2B in FIG. 2A.;

FIG. 2C is a cross-sectional view of a guide catheter tip taken along lines 2C—2C in FIG. 2A;

FIG. 4A is an alternative embodiment showing a cross sectional view of a guide catheter tip manufactured in accordance with the present invention;

FIG. 4B is a cross-sectional view of the proximal portion of a guide catheter tip taken along lines 4B—4B in FIG. 4A.;

FIG. 4C is a cross-sectional view of the guide catheter tip taken along lines 4C—4C in FIG. 4A;

FIG. 5A is another alternative embodiment showing a cross sectional view of a guide catheter tip manufactured in accordance with the present invention;

FIG. 5B is a cross-sectional view of the proximal portion of a guide catheter tip taken along lines 5B—5B in FIG. 5A.;

FIG. 5C is a cross-sectional view of the guide catheter tip taken along lines 5C—5C in FIG. 5A;

DETAILED DESCRIPTION OF THE PREFERRED EMBODIMENTS

Figure 1:
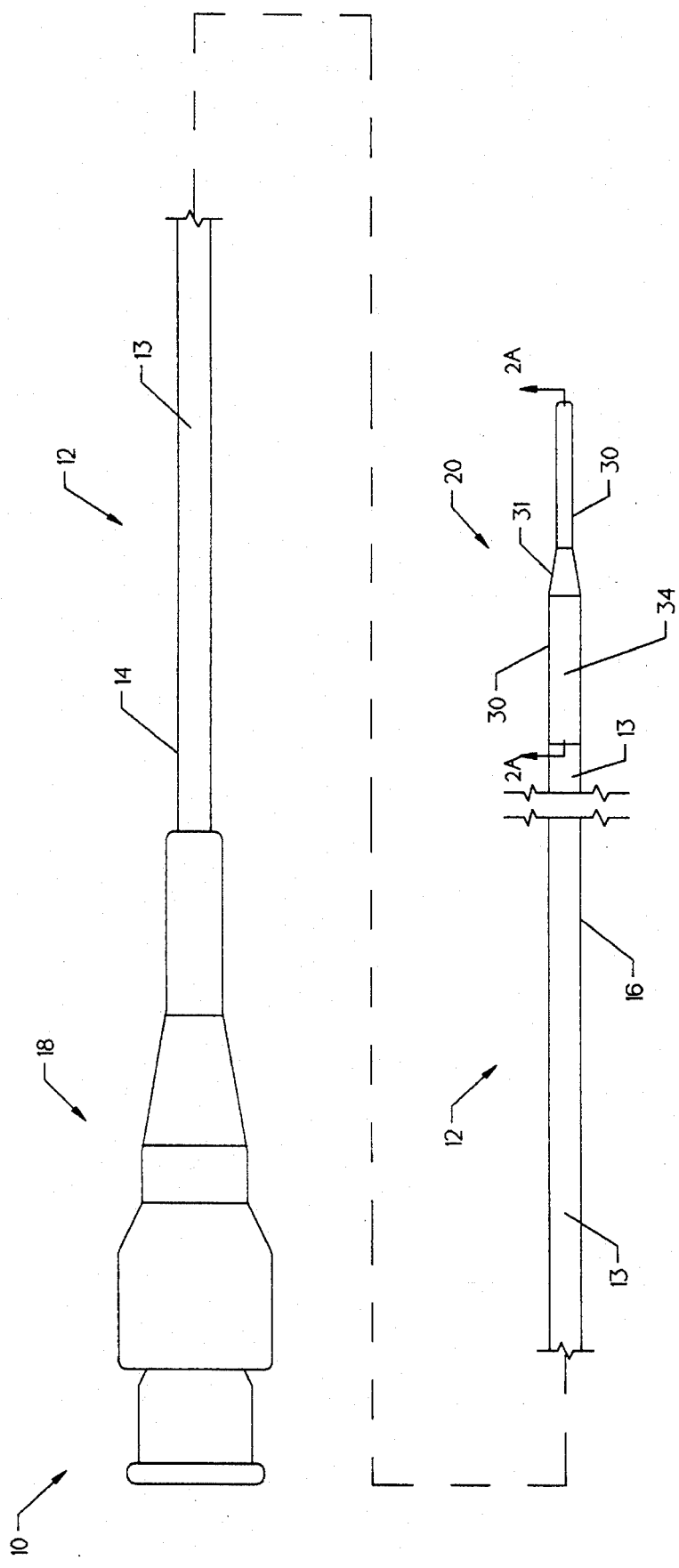
FIG. 1 is a perspective view of a guide catheter having a tubular member manufactured in accordance with the method of the present invention.

Guide, diagnostic, angiographic and balloon dilatation catheters are well known for use in coronary diagnostic procedures and percutaneous transluminal coronary angioplasty (PTCA) procedures. FIG. 1 shows a catheter assembly generally at 10. The catheter 10 includes a shaft 12, having a proximal end 14 and a distal end 16. Operably connected to the proximal end 14 of the shaft 12 is a hub assembly 18. Operably connected to the distal end 16 of the shaft 12 is a soft tip 20.

The shaft 12 is multi-layered, formed of an inner layer, a structural layer, and an outer layer (layers not shown). The inner layer is extruded polyurethane in the form of a tubular member defining a longitudinally extending lumen (not shown). The structural layer is formed over the inner layer and includes helically braided strands of stainless steel which may be embedded in the inner layer. The multi-layered assembly results in a relatively stiff catheter shaft, providing the responsiveness necessary for proximal manipulization of the catheter shaft for guiding the catheter through a patient's tortuous vascular system.

The hub assembly 18 is injection molded over a portion of the shaft 12 proximal end 14. The hub assembly 18 is designed to mate with additional assemblies (not shown) for communication with catheter shaft 12. Such assemblies include Y-adapter and manifold assemblies for use in diagnostic procedures such as die delivery, flushing, and arterial pressure monitoring, and PTCA procedures for delivery of a balloon system to the coronary region having the stenosis to be dilatated.

In operation, catheter 10 is introduced over a guide wire through a previously placed femoral introducer sheath and advanced up to the aortic arch. The guide wire is then removed. In PTCA procedures, catheter 10 is advanced and maneuvered until the catheter soft tip 20 is engaged in the ostium of the coronary to be dilatated. With the catheter 10 in place, a balloon system may now be positioned across the stenosis marked for treatment.

Referring to FIG. 1 and FIG. 2A, which is a sectional view of the catheter 10 soft tip 20 shown in FIG. 1, the catheter 10 soft tip 20 includes a proximal section 30, a transitional section 31, and a distal section 32. A lumen 34 extends longitudinally through the proximal section 30, transitional section 31, and distal section 32. Soft tip 20 is formed of a soft extruded polymeric material, such as a polyether blocked amide or PEBA, for atraumatic movement of the catheter 10 through a patient's delicate arterial anatomy.

Soft tip 20 varies in dimension from the proximal section 30 to the distal section 32. In general, the proximal section 30 of soft tip 20 is of a larger diameter than the distal end 32. The narrower distal end 32 provides improved catheter steerability and less traumatic movement of the catheter as it moves through the arterial anatomy of the patient. Additionally, narrowed distal section 32 provides for safer ostial engagement of the coronary artery to be dilatated.

FIG. 2B is a cross-sectional view of proximal section 30 of FIG. 2A, and FIG. 2C is a cross-sectional view of distal section 32 of FIG. 2A. In one preferred embodiment, proximal section 30 is approximately the same length as distal section 32, and has an outside diameter OD1 and inside diameter ID1. Transitional section 31 transitions the dimensional characteristics of proximal section 30 to the dimensional characteristics of distal section 32.

Distal section 32 has an outside diameter OD2 and an inside diameter ID2. In one preferred embodiment, outside diameter OD1 is larger than outside diameter OD2, and inside diameter OD1 is equal to inside diameter ID2. Alternatively, outside diameter OD1 may be equal or smaller than outside diameter OD2, and inside diameter ID1 may be larger or smaller than inside diameter ID2.

Figure 3:
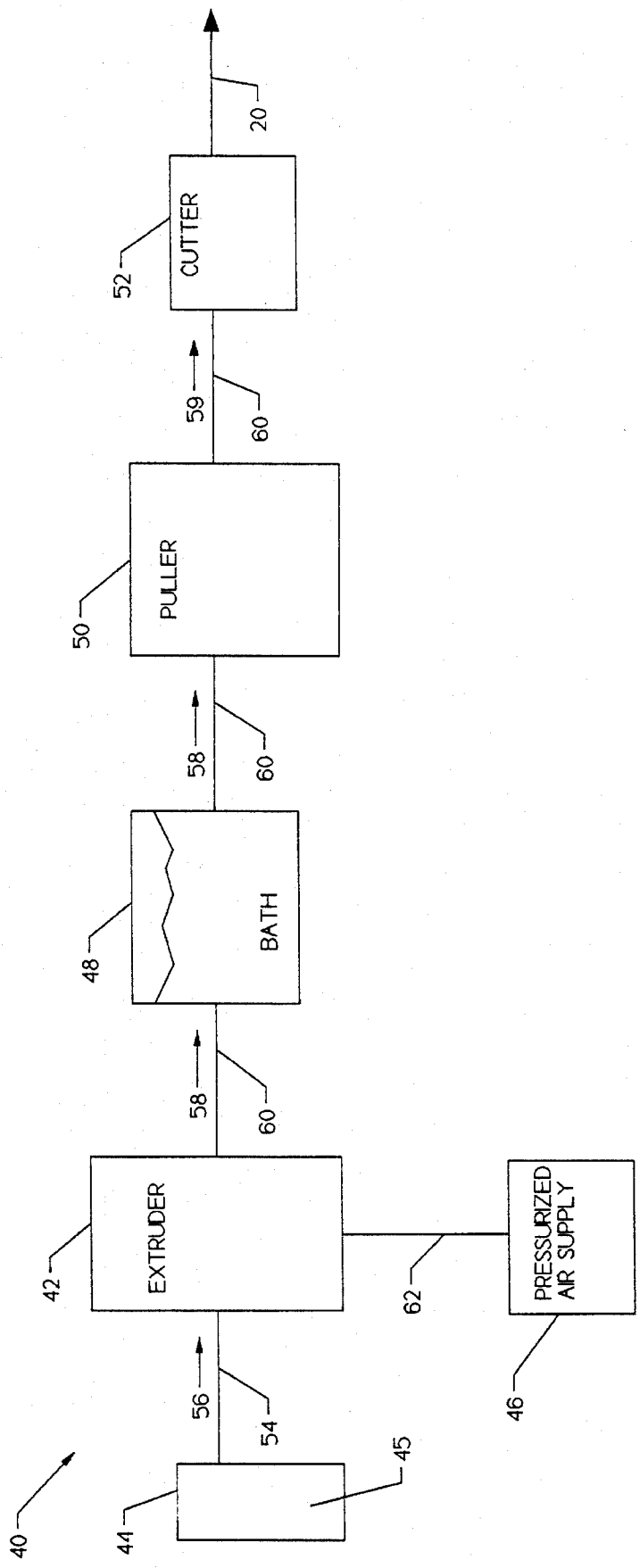
FIG. 3 is a schematic view illustrating a method of manufacturing a dimensionally variable tubular member in accordance with the present invention.

The dimensionally varying tip 20 shown in FIGS. 1, 2A, 2B, and 2C is made using the manufacturing method of the present invention shown in schematic form in FIG. 3. This manufacturing method allows dimensionally varying tubular members, such as tip 20 in FIGS. 1 and 2A–2C, to be manufactured to exact specifications to meet desired operational and performance characteristics.

Referring to FIG. 3, the process of forming a dimensionally variable tubular member is shown generally at 40. The process 40 includes extruder 42, material supply 44, pressurized air or gas supply 46, cool water bath 48, puller 50, and cutter 52.

Material supply 44 supplies a soft polymeric material 45, such as PEBA, to extruder 42 indicated at 54. Extruder 42 includes a rotating screw mechanism (not shown) for pulling the material 45 from material supply 44 into extruder 42 at a desired rate indicated by directional arrow 56.

Within extruder 42, the material 45 is heated and pushed through a tip and die set designed for tubing extrusions (not shown) to form tubular member 60. Next, the hot extruded tubular member 60 is pulled through cool water bath 48 by puller 50, indicated by directional arrows 58.

Puller 50 is a variable speed puller. In a typical extrusion process, extruded tubing is pulled from the extruder at a constant pull speed. Variable speed puller 50 allows extruded tubular member 60 to be pulled from extruder 42 at a desired or variable speed. By varying the speed at which the extruded tubular member is pulled from extruder 42, the dimensional characteristics of the tubular member are controlled and changed.

Increasing and decreasing the rate of variable speed puller 50 changes volume of material extruded in a given length of tubing. Referring to FIG. 2A, by pulling tubular member 60 at a first, faster rate, distal section 32 results. Distal section 32 has a relatively narrow outside diameter OD2, with a relatively less amount of extruded material 37. In contrast, proximal section 30 is formed by pulling tubular member 60 at a faster rate, resulting in a relatively larger outside diameter OD1 with a greater amount of extruded material 35.

Air or gas supply 46 supplies air or gas to extruder 42, indicated at 62. Air is utilized in a preferred embodiment. In a typical extrusion process, pressurized air is supplied to an extruder at a constant air pressure. In accordance with the present invention, pressurized air supply 46, which is coupled to the extruder 42 tip and die set, may vary the air pressure and air volume supplied to extruder 42. Increasing or decreasing the air pressure supplied to extruder 42 varies the dimensional characteristics of extruded tubular member 60. Additionally, increasing or decreasing the volume of air supplied to extruder 42 varies the dimensional characteristics of extruded tubular member 60.

By changing the volume and/or pressure of the pressurized air supply 62, the inside diameter of lumen 34 may be varied. An increase in air pressure or volume may be used to maintain a constant inside diameter of lumen 34 while the speed of puller 60 is increased, or an increase in pressure or volume may be used to achieve a change to a larger inside diameter of lumen 34.

After passing through puller 50, tubular member 60 moves through cutter 52, indicated by directional arrow 59. Cutter 52 cuts tubular member 60 into desired lengths, resulting in the end product, a dimensionally varying tubular member, such as tip 20.

Referring to FIGS. 2A–2C, the varied dimensional characteristics of soft tip 20 is formed by using process 40 in accordance with the present invention. Tubular member 60 is pulled from extruder 42 at a first desired rate and pressurized air supply to achieve the dimensional characteristics of distal section 32. Next, the pulling speed of puller 50 and the air pressure supplied by pressurized air supply 46 to extruder 42 are changed. This process change is reflected in the resulting soft tip 20 transitional section 31. The changed pulling rate and pressurized air supply volume or pressure results in the dimensional characteristics of proximal section 30. The varied dimensional characteristics of soft tip 20 results in a proximal section 30 having a large outside diameter OD1 relative to distal section 32 outside diameter OD2, and a larger volume of extruded material, indicated at 35, than distal section 32, indicated at 37.

By using the process 40, it is recognized that a variety of soft tips having varying dimensional characteristics may be manufactured to achieve desired performance. In an alternative embodiment shown in FIGS. 4A–4C, the air pressure supplied to extruder 42 and the puller speed 50 were varied to achieve a proximal section 30 having outside diameter OD1 and a distal section 32 having a smaller outside diameter OD2, and a proximal section 30 having a inside diameter ID1 which is larger than distal section 32 inside diameter ID2.

FIGS. 5A–5C show another embodiment of a distal tip 20 manufactured by process 40. In this embodiment, proximal section 30 outside diameter OD1 is larger than distal section 32 outside diameter OD2. Proximal section 30 inside diameter ID1 is larger than distal section 32 inside diameter ID2. Also, proximal section 30 inside diameter ID1 is larger than distal section 32 outside diameter OD2.

By using the novel process of the present invention, dimensionally variable tubular members may be formed to desired specifications to meet required operational and performance characteristics without sacrificing the structural integrity of the tubular member. The dimensionally variable tips manufactured in accordance with the present invention allow for atraumatic movement of the catheter through the patient's arterial system, while improving steerability and providing for a safer ostial engagement. Additionally, the inside diameter of the catheter tip may be varied to improve catheter performance characteristics and be compatible with other diagnostic and PTCA systems.

Figure 6:
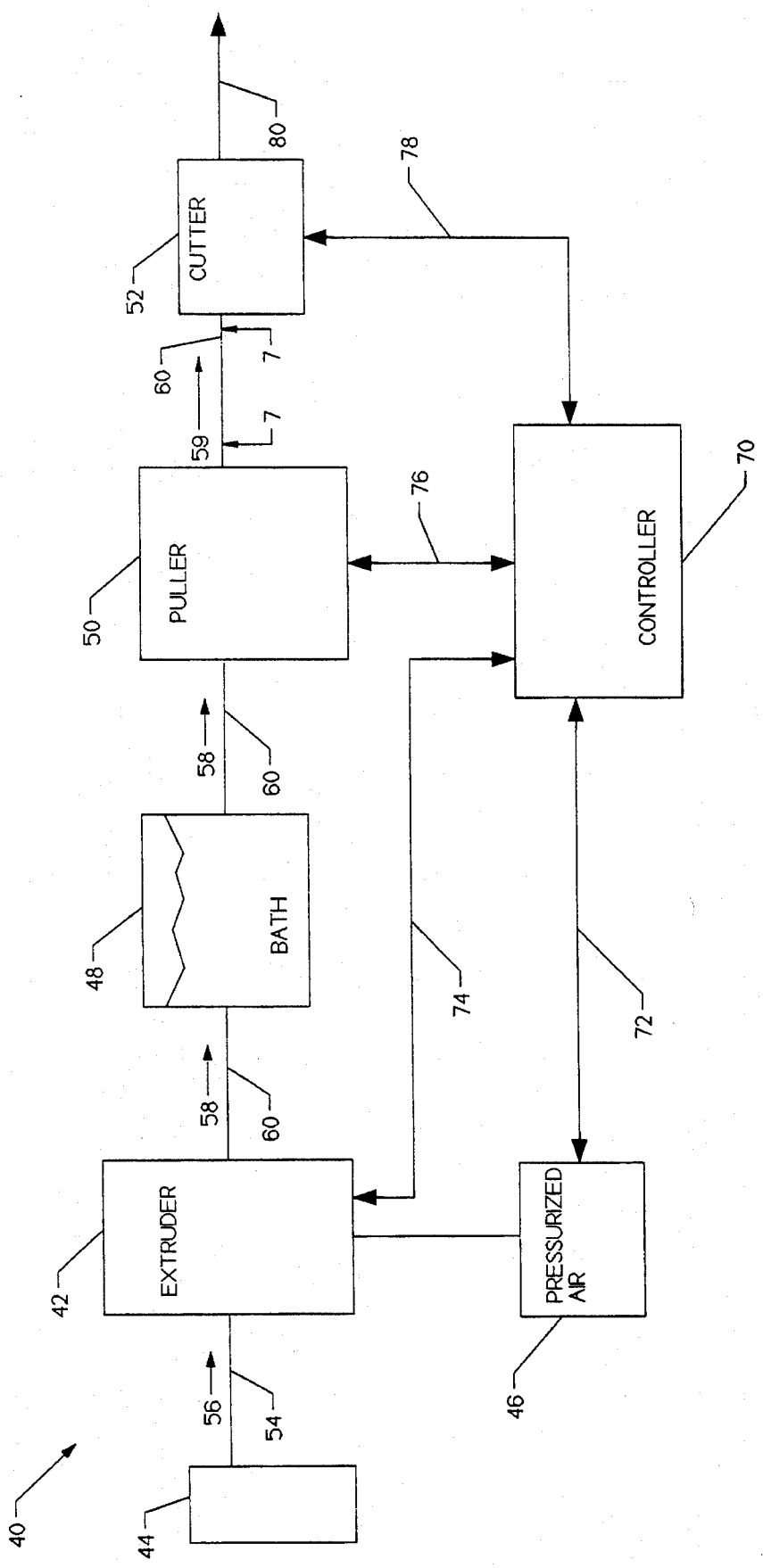
FIG. 6 is a schematic view illustrating another method of manufacturing a dimensionally variable tubular member in accordance with the present invention.

FIG. 6 shows a preferred embodiment of the present invention, which further includes a controller 70. Controller 70 may be a switching device or other device capable of controlling a sequence of logical operations, such as a computer, logic gates, switches or microprocessor based control systems. In a preferred embodiment, controller 70 is a microprocessor based programmable controller which provides centralized control of process 40.

Controller 70 is electrically coupled to pressurized air supply 46 (72), extruder 42 (74), puller 50 (76), and cutter 52 (78). In operation, controller 70 is programmable to control the air pressure and air volume supplied by pressurized air supply 46; the rate material is supplied to extruder 42; the speed of puller 50; and the timing of cutter 52 to achieve exacting dimensional characteristics for a catheter tip.

Figure 7:
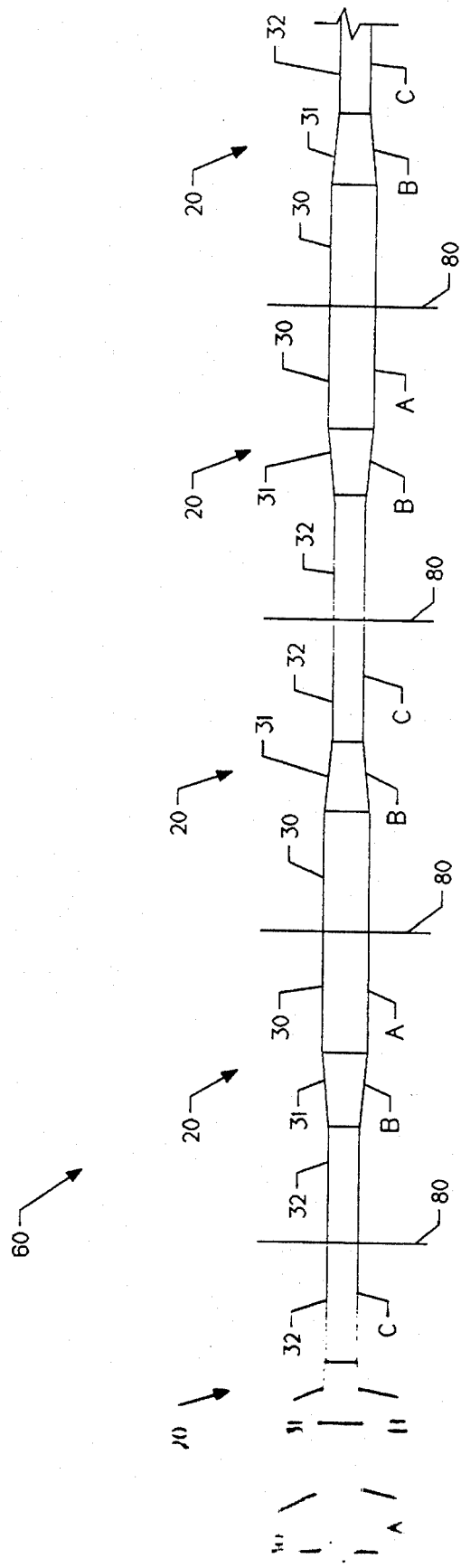
FIG. 7 is a side view of a dimensionally variable tubular member manufactured in accordance with the present invention taken along lines 7—7 of FIG. 6.

In one preferred embodiment, controller 70 is programmed to provide a tubular member 60 having the dimensional characteristics shown in FIG. 7. Controller 70 controls pressurized air supply 46, extruder 42, and puller 50, to produce a tubular member having dimensionally varied sections A, B, and C. Section A is a larger dimensioned tubular member, which transitions through section B, to a smaller tubular member of section C. In one preferred embodiment, section A and C are three inches in length, and section B is less than one inch in length.

Controller 70 times cutter 52 to efficiently cut at points 80, the continuous tubular member 60 into dimensionally precise soft catheter tips 20. After passing tubular member 60 through cutter 52, each individual soft tip 20 includes a proximal section 30, a transitional section 31, and a distal section 32.

By controlling the air or gas pressure supplied to extruder 42 and the speed of puller 50, tubular members may be formed having exacting, but varying dimensional characteristics. The inside and outside diameters of proximal sections 30 and 32 may be changed as desired, and also the lengths of proximal section 30 and distal section 32. The tubular member may contain multiple changes in dimensions for each catheter or tubular member formed.

Additionally, the length of transition section 31 and the volume of material and thickness of the tubular member walls may also be controlled. In one embodiment, transitional section 31 is programmed to be less than one inch in length.

The process of the present invention allows dimensionally variable tubular members to be formed to desired specifications to meet required operational and performance characteristics without sacrificing the structural integrity of the tubular member. The dimensionally variable tips manufactured in accordance with the present invention allow for atraumatic movement of the catheter through the patient's arterial system, while improving steerability and providing for a safer ostial engagement. Additionally, the inside diameter of the catheter may be varied to improve catheter performance characteristics and be compatible with other catheter diagnostic and PTCA systems.

Figure 8A:
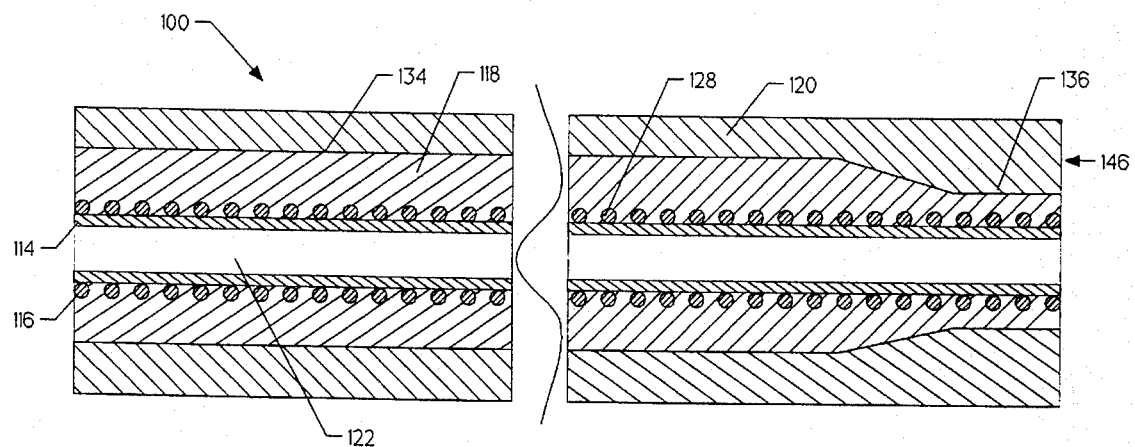
FIGS. 8A–8C illustrate in cross-sectional view another embodiment manufactured in accordance with the present invention.
Figure 8B:
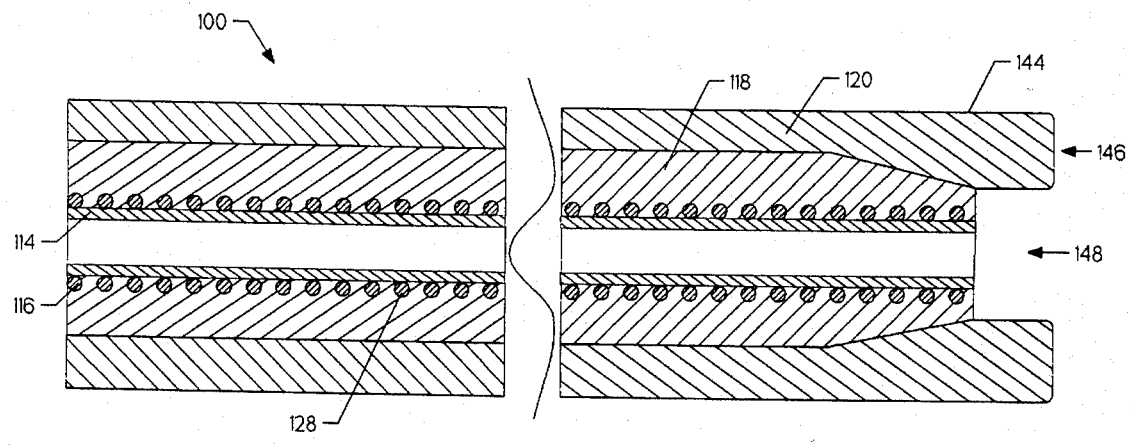
Figure 8C:
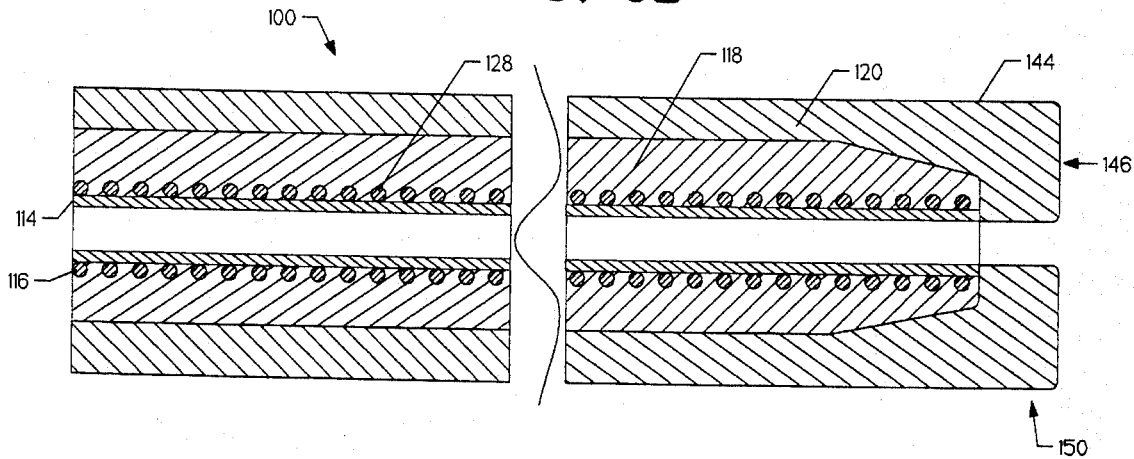

Yet another embodiment of the present invention is shown in FIGS. 8A–8C. In FIG. 8A, a catheter is shown in an enlarged cross-sectional view generally at 100. In a preferred embodiment, the catheter 100 is used as a guide, diagnostic, or angiographic catheter, and can be similar to the catheter 10 shown in FIG. 1. Catheter 100 is multi-layered, and may include a base layer 114, a structural layer 116, a rigid layer 118, and a soft layer 120.

Figure 9:
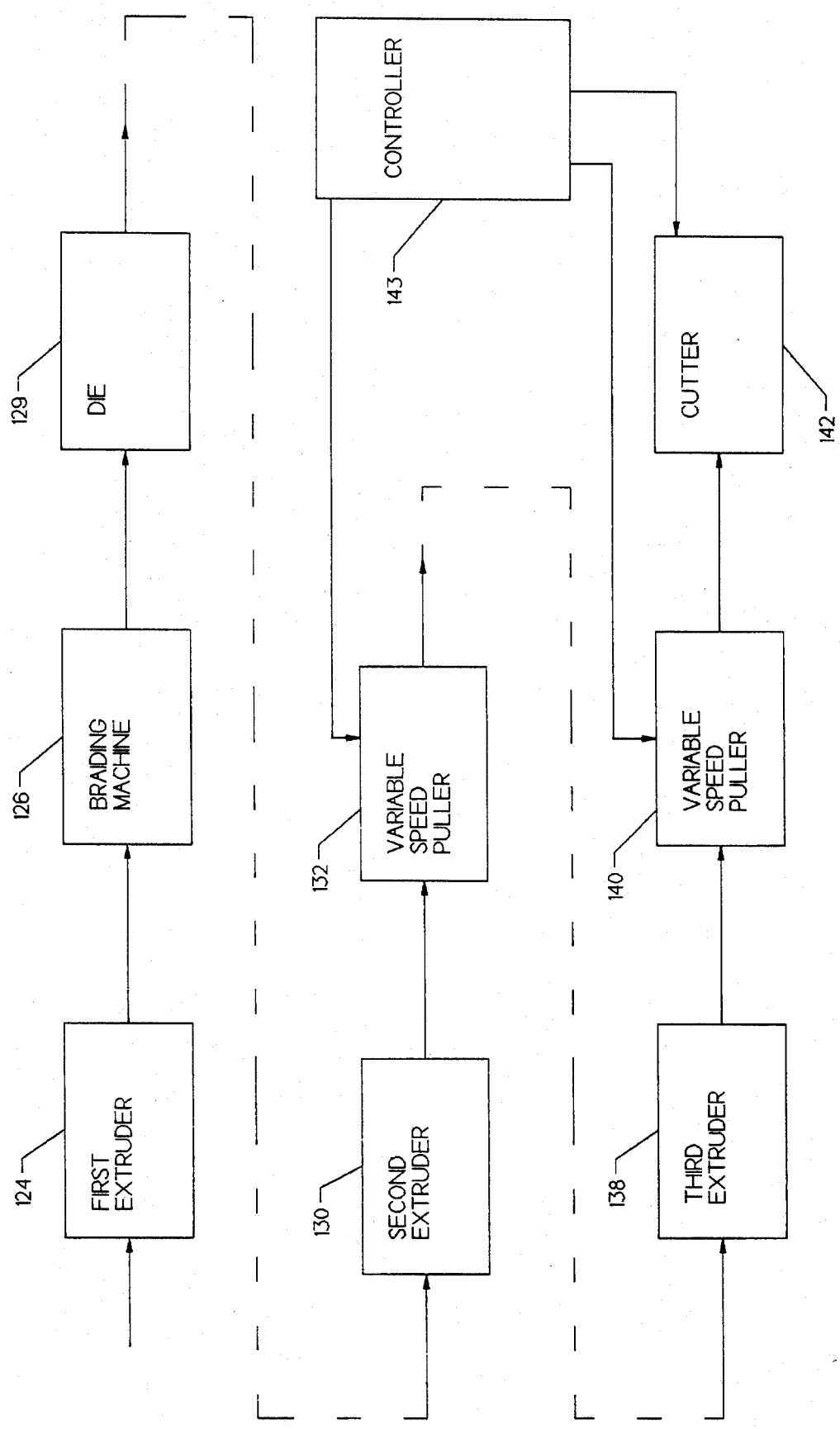
FIG. 9 is a schematic view illustrating another method of manufacturing a dimensionally variable tubular member in accordance with the present invention.

In one preferred embodiment, the catheter 100 is formed using the process shown in schematic view in FIG. 9. Base layer 114 is formed over a mandrel 122, which is pulled through or from a first extruder 124. First extruder 124 extrudes a suitable plastic onto mandrel 122 using a convention extrusion process. In one preferred embodiment, mandrel 122 is formed of a silver-coated copper wire, and base layer 114 is formed of a thin coat of semi-soft plastic elastomeric material, such as polytetraphloralethylene (PTFE), having a lubricous inner surface. Mandrel 122 forms base layer 114 in a tubular shape, in a size such that later removal of mandrel 122 will provide catheter 100 with a lumen sized to carry various intravascular catheter devices.

Next, catheter 100 is cooled and past through a machine 126 for braiding structural layer 116 on base layer 114. As catheter 100 passes through machine 126, strands 128 are tightly braided onto base layer 114 to form structural layer 116. It is recognized that machine 126 may be a conventional wrapping device which wraps the strands 128 around base layer 114 by braiding or helical wrapping. Catheter 100, having structural layer 116, may be passed through a heated die 129 for at least partially embedding structural layer 116 in base layer 114.

Catheter 100 is then pulled through or from a second extruder 130 by a variable speed puller 132 forming a dimensionally variable rigid layer 118. In one preferred embodiment, rigid layer 118 is formed of a rigid polymer. By pulling catheter 100 through or from second extruder 130 at varying speeds, the thickness of rigid layer 118 is varied, resulting in a dimensionally variable rigid layer 118. As shown in FIG. 8A, pulling catheter 100 through or from second extruder 130 at a first speed, results in rigid layer 118 having a larger amount of material deposited over structural layer 116 indicated at 134; and pulling catheter 100 through or from second extruder 130 at a second faster speed, results in rigid layer 118 having a relatively smaller amount of material placed over structural layer 116, indicated at 136.

Catheter 100 is next passed through or from a third extruder 138 forming a smooth, soft layer 120 over rigid layer 118. In one preferred embodiment, soft layer 120 is formed of a PEBA blend or an elastomeric polyurethane.

Soft layer 120 provides a thin, smooth, soft cover layer for passing the catheter through a patient's tortious vascular system and for atraumatic ostial engagement.

The second variable speed puller 140 pull rate may be varied to provide catheter 100 with a uniform outer diameter as shown in FIG. 8A. Alternatively, the speed of second variable speed puller 140 may be varied to provide catheter 100 with a dimensionally variable outer diameter. In the preferred embodiment shown in FIG. 8A, the speed of second variable speed puller 140 is programmed such that a smaller amount of material 120 is deposited over the area of rigid layer 118 having more material (134), and a greater amount of material is deposited over rigid layer 118 having less material (136), resulting in a catheter 100 of uniform outer diameter. A multi-layer continuous length of catheter 100 is now formed.

Cutter 142 then cuts catheter 100 into desired catheter lengths for use in guide, diagnostic and angiographic catheter procedures.

In a preferred embodiment, shown in FIG. 9, the above process is programmably controlled by a controller 143. It is recognized that controller 143 may be a device capable of performing logical operations, such as a microprocessor based controller, computer, relays, or a sequence of logic gates. In a preferred embodiment, controller 143 is a microprocessor based programmable controller. Controller 143 may communicate with each manufacturing process device, including variable speed puller 132, variable speed puller 140, and cutter 142 as shown in FIG. 9, for manufacturing catheter 100 to desired varying dimensional characteristics.

Figure 9A:
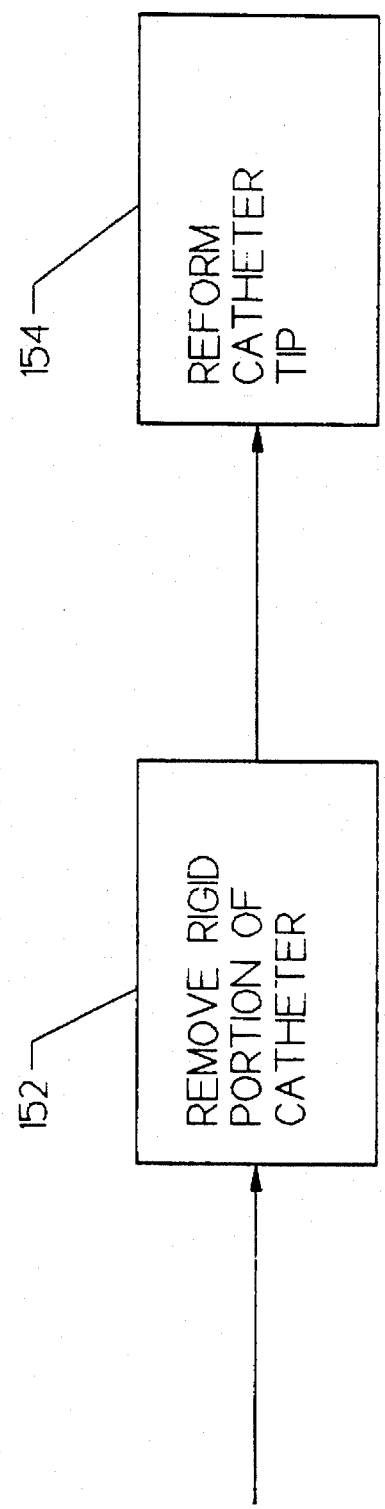
FIG. 9A is a schematic view illustrating an additional step of the method of manufacturing shown in FIG. 9.
Figure 7:
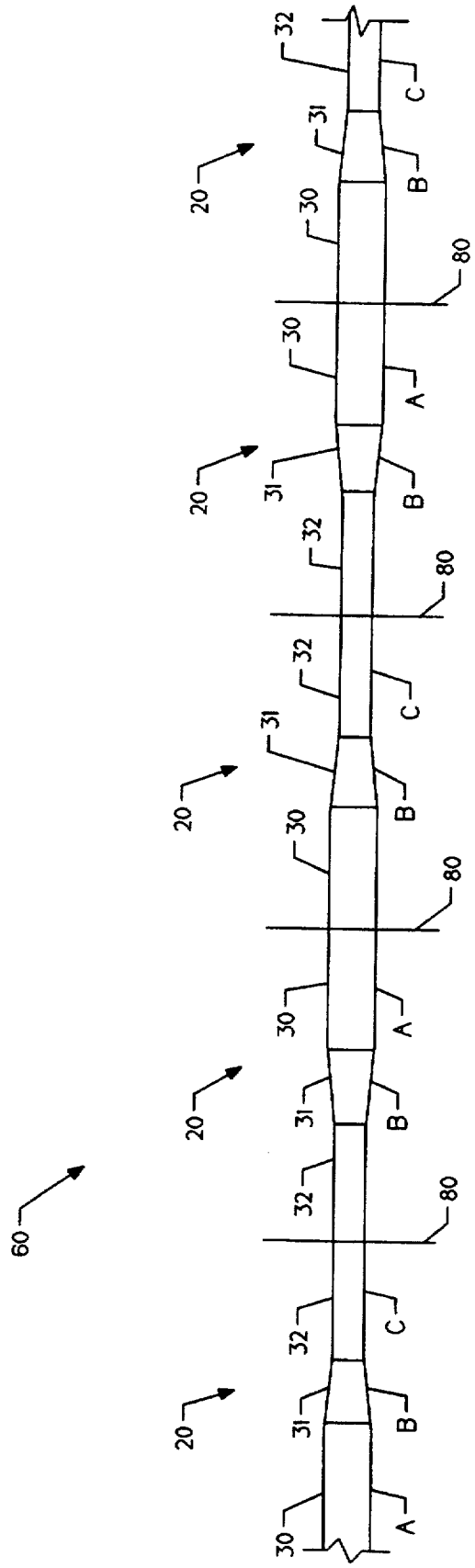

As shown in FIGS. 8B and 8C, and schematically in FIG. 9A, a soft, non-fused, atraumatic catheter tip 144 may be formed by removing the base layer 114, structural layer 116, and rigid layer 118 from the distal end 146 of catheter tip 144 (indicated schematically at 152). In one preferred embodiment, layers 114, 116, and 118 are removed through conventional counter bore methods, indicated at 148. The remaining soft layer 120 would be reformed (indicated schematically at 154), such as by a heating process, into a soft integral tip 150 for allowing atraumatic movement of catheter 100 through a patient's vascular system and for safer ostial engagement.

This embodiment of the present invention allows for a soft distal catheter tip, while removing two typical bonds and several conventional catheter manufacturing process steps.

It will be understood that this disclosure is, in many respects, only illustrative. It is recognized that the method in accordance with the present invention may be used to manufacture dimensionally variable tubular members for use in manufacturing catheter shafts, catheter tips, fuseless catheter systems, and other products where dimensionally varying characteristics are desirable. Changes may be made in details, particularly in matters of shape, size, material, and arrangement of parts, without exceeding the scope of the invention. Accordingly, the scope of the invention is as defined in the language of the appended claims.

What is claimed is:

1. An apparatus for performing the process of manufacturing a catheter having a dimensionally variable tip region for use in catheterization procedures, the apparatus comprising:

a. extrusion means for extruding a tubular member, the tubular member having a lumen extending longitudinally therethrough and including the tip region;

b. means for selectively varying an inside diameter of the tubular member, including means for providing gas to the lumen at a selectively variable rate;

c. means for selectively varying an outside diameter of the tubular member independent of the means for selectively varying an inside diameter of the tubular member, including means for pulling the tubular member from the extrusion means at a selectively variable speed; and d. wherein the tip region includes a first portion and a second portion, the first portion having a first outside diameter formed by the pulling means pulling the tubular member from the extrusion means at a first speed, and the second portion having a second outside diameter smaller than the first outside diameter formed by the pulling means pulling the tubular member from the extrusion means at a second speed.

2. The apparatus of claim 1, wherein the pulling means includes a puller coupled to a variable speed drive.

3. The apparatus of claim 1, further wherein the tip region includes the first portion having a first inside diameter formed by the means for providing gas to the lumen at a first rate, and the second portion having a second inside diameter formed by the means for providing gas to the lumen at a second rate.

4. The apparatus of claim 1, wherein the selectively variably rate includes providing gas at a selectively variable volume and a selectively variable pressure.

5. The apparatus of claim 1, further including means for supplying material to the extrusion means for forming the tubular member, and means for selectively varying the rate at which material enters the extrusion means.

6. The apparatus of claim 1, further including means for selectively cutting the tubular member into desired lengths.

7. The apparatus of claim 1, further including control means for providing signals to the means for selectively varying the inside diameter of the tubular member representative of desired tubular member dimensional characteristics.

8. A process for forming a dimensionally variable catheter having a tip region including a proximal portion and a distal portion for use in catheterization procedures, the process comprising the steps of:

a. extruding a tubular member having a lumen extending longitudinally therethrough by passing an extrudable material through an extruder;

b. moving the tubular member from the extruder at a desired speed;

c. providing air to the lumen from an air supply at a desired rate, including a first pressure and a first volume; and d. changing an inside diameter of the tubular member to form the catheter tip region by selectively changing the rate at which air is supplied to the lumen.

9. The process of claim 8, wherein the rate air is supplied to the lumen is selectively controlled by a controller.

10. The process of claim 8, wherein by changing the rate at which air is supplied to the lumen, the inside diameter is changed to a second inside diameter within a catheter length of one inch.

11. The process of claim 8, wherein forming the catheter tip region further comprises the step of:

changing an outside diameter of the tubular member within the catheter tip region independent of changing the inside diameter, by changing the speed at which the tubular member moves from the extruder.

12. The process of claim 11, wherein the speed is selectively controlled by a controller.

13. The process of claim 11, wherein by changing the speed at which the material is pulled from the extruder, the outside diameter is changed to a second outside diameter within a length of one inch.

14. The process of claim 8, further comprising the step of:

cutting the tubular member into desired lengths.

15. The process of claim 14, wherein cutting the tubular member into desired lengths is selectively controlled by a controller.

16. A process for forming a dimensionally variable tubular member having multiple layers for use with catheterization procedures, the dimensionally variable tubular member having a tip region, the process comprising the steps of:

a. extruding a dimensionally varying tubular first layer by controlling the speed at which the first layer is extruded;

b. extruding a dimensionally varying tubular second layer over the first layer by controlling the speed at which the second layer is extruded; and c. removing a portion of the first layer below the second layer at a distal end of the tubular member to form the tip region.

17. The process of claim 16, further comprising the step of:

a. reforming the distal end of the tubular member.

18. The process of claim 17, wherein the distal end is reformed through a heating process.

19. The process of claim 16, further comprising the steps of:

a. forming a tubular member over a mandrel; and b. forming a structural layer over the tubular member, wherein the first layer is formed over the structural layer.

* * * * *

UNITED STATES PATENT AND TRADEMARK OFFICE
CERTIFICATE OF CORRECTION

PATENT NO. : 5,614,136

DATED : March 25, 1997

INVENTOR(S) : Pepin et al

It is certified that error appears in the above-identified patent and that said Letters Patent is hereby corrected as shown below:

In the drawings, Sheet 6 of 9, consisting of Fig. 7, should be deleted and replace therefor with the corrected Fig. 7, as shown on the attached page.

Signed and Sealed this

Seventeenth Day of June, 1997

Attest:

BRUCE LEHMAN

*Attesting Officer*     *Commissioner of Patents and Trademarks*